(12) United States Patent
Barbera-Guillem (10) Patent No.: US 7,041,362 B2
(45) Date of Patent: *May 9, 2006

(54) METHODS FOR IDENTIFICATION AND VERIFICATION

(75) Inventor: Emilio Barbera-Guillem, Powell, OH (US)

(73) Assignee: Invitrogen Corp., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/842,327

(22) Filed: May 10, 2004

(65) Prior Publication Data

US 2004/0203170 A1    Oct. 14, 2004

Related U.S. Application Data

(63) Continuation of application No. 09/436,145, filed on Nov. 9, 1999, now abandoned.

(60) Provisional application No. 60/107,829, filed on Nov. 10, 1998.

(51) Int. Cl.
  *B32B 5/16* (2006.01)
  *B32B 9/00* (2006.01)
  *B32B 31/00* (2006.01)
  *B32B 33/00* (2006.01)

(52) U.S. Cl. .................. 428/206; 428/207; 428/323; 428/916

(58) Field of Classification Search .............. 238/72, 238/92; 356/71; 523/200; 106/31.15, 452; 427/212, 157; 428/323, 403, 404, 916, 206, 428/207
See application file for complete search history.

(56) References Cited

U.S. PATENT DOCUMENTS

| 4,767,205 A | 8/1988 | Schwartz et al. |
| 5,289,547 A | 2/1994 | Ligas |
| 6,575,155 B1 | 6/2003 | Brennan |
| 6,576,155 B1 | 6/2003 | Barbera-Guillem |

(Continued)

OTHER PUBLICATIONS

Jacoby, "Quantum Dots meet Biomolecules"; C&EN, 1998, Sep. 28, 1998; pp. 8.

Emory, et al.; "Direct Observation of Size-Dependent Optical Enhancement in Single Metal Nanoparticles"; 1998, J.Am. Chem. Soc. vol. 12; 8009-8010.

Service; "Semiconductor Beacons Light Up Cell Structure" Sceince, 1998, Sep. 25, 1998, vol. 281; pp. 1930-1931.

(Continued)

*Primary Examiner*—Ramsey Zacharia (74) *Attorney, Agent, or Firm*—Raymond A. Miller; Pepper Hamilton LLP (57) ABSTRACT

An identifiable code pattern, a method of providing a carrier material with an identifiable code pattern, and a method for detecting an identifiable code pattern are based on applying water-soluble nanocrystals to carrier materials in a spatially arranged format that can be detected by exposing the identifiable code pattern to an excitation light source in exciting the water-soluble nanocrystals, and detecting any fluorescence peaks emitted from the excited water-soluble nanocrystals using a detection system.

13 Claims, 3 Drawing Sheets

U.S. PATENT DOCUMENTS 5,592,561 A    1/1997    Moore
5,795,379 A    8/1998    Schwenk

OTHER PUBLICATIONS

Chan, et al.; "Quantum Dot Bioconjugates for Ultra Sensitive Nonisotopic Detection" Science, Sep. 25, 1998; vol. 281; pp. 2016-2018.

Bruchez, et al.; Semiconductor Nanocrystals as Fluorescent Biological Labels; Science, 1998, Sep. 25, 1998; vol. 281; 2013-2015.
Jacoby, C&EN, 1998, Sep. 28, p. 8.
Han et al., J. Am. Chem. Soc. 120:8009-8010, 1998.
Service, Science 28:1930-1931, 1998.
Bruchwz et al, Science 281:2013-2015, 1998.
Chan et al, Science 281:2016-2018, 1998.

GYGYYOGRORYRRGYRYGGOYYOORGRRGG

FIG. 5

METHODS FOR IDENTIFICATION AND VERIFICATION

CROSS-REFERENCE TO RELATED APPLICATIONS

This application is a continuation of U.S. patent application Ser. No. 09/436,145, filed Nov. 9, 1999, now abandon, which claims the benefit and priority of U.S. Provisional Application Ser. No. 60/107,829, filed Nov. 9, 1998, the contents of each incorporated in this application in their entirety by reference.

FIELD OF INVENTION

This invention relates to application of water-soluble nanocrystals to carrier materials to provide an identifying code pattern comprising discrete, detectable signals which may be detected for identification and/or verification purposes.

BACKGROUND OF THE INVENTION

Counterfeiting and diversion continue to be a significant problems in the area of consumer goods. Various marking, authenticating, and identifying schemes have been devised to authenticate and/or track the distribution of goods. For example, U.S. Pat. No. 5,289,547 discloses a method for authenticating articles by incorporating into a carrier composition a mixture of at least two photochromic compounds having different characteristics including absorption maxima during an activated state and color. Discriminating between the different characteristics of the photochromic compounds used, enables the method of identification. U.S. Pat. No. 4,767,205 discloses a code identification by use of microparticles of precise size, shape, and color, and by applying such particles in combinations to an item to be marked. The color identifying system disclosed comprises recognizing and identifying with a light microscope the code comprised of the microparticles. Other methods and compositions have been described for authentication, including inks or dyes or paints that impart photoluminescent or ultraviolet properties; and geometric positioning of threads or strips or particles which are either visibly detectable or detectable by x-ray.

There remains a need to enable efficient labeling or encoding of large numbers of items such as sensitive documents, bank cards, credit cards, controlled access cards, currency, fine art, goods wherein the distribution of which is desirably to be controlled by tracking, objects of commercial value, and such other items which are desired to be tracked or identified. Desirably, the compositions and methods would not be easily duplicated.

SUMMARY OF THE INVENTION

The present invention provides compositions comprising nanocrystals that can be used to establish an identifiable code pattern. The compositions comprise water-soluble quantum dots which can be prepared in several uniform sizes, wherein the water soluble quantum dots can be excited with a single wavelength of light resulting in a detectable luminescence and/or fluorescence emission of high quantum yield. However, a discrete luminescence a of narrow bandwidth and of a particular color emitted by a water-soluble quantum dot is primarily size-dependent. Thus, an identifiable code pattern may comprise a combination of separate deposits or localizations of water-soluble quantum dots spatially arranged in or on the carrier material, wherein each deposit or localization may comprise a plurality of water-soluble quantum dots of a specific uniform size.

Thus, in a method of detecting an identifiable code pattern comprised of water-soluble nanocrystals according to the present invention, the carrier material being analyzed for the presence or absence of an identifiable code pattern is briefly illuminated with a light source comprising the appropriate excitation wavelength. On exposure to such light, the water-soluble nanocrystals comprising the identifiable code pattern will, if present, emit a discrete fluorescence peak of narrow bandwidth and of a particular color (one color) or discrete fluorescence peaks (multicolor), thereby making the identifiable code pattern detectable. The user may quickly detect the identifiable code pattern encoded by the spatial arranged deposits or localizations of water-soluble nanocrystals using a detection system for detecting the one or more discrete fluorescence peaks emitted by the excited water-soluble nanocrystals comprising the identifiable code pattern, if present. By detecting the one or more discrete fluorescence peaks, the identifiable code pattern may be identified, and a determination may be made as to one or more of the identity or authenticity or localization of the carrier material. The identifiable code pattern may comprise a mark or symbol or specific arrangement of deposits or localizations of the water-soluble nanocrystals. Detection may be by detection system comprising a scanner or reader which can detect and distinguish discrete fluorescence peaks. Preferably, the detection system also has a means of directly comparing the detected identifiable code pattern identified with a database of authenticated codes to confirm that the code pattern so identified is authentic. Identification of an identifiable code pattern may further comprise reading of data encoded by the code pattern, which can be decoded by the detection system in a process of identifying or tracking the carrier material (as analogous to a barcode).

The above and other objects, features, and advantages of the present invention will be apparent in the following Detailed Description of the Invention when read in conjunction with the accompanying drawings in which reference letters denote the same or similar parts throughout the several illustrated views and embodiments.

DETAILED DESCRIPTION OF THE INVENTION

Definitions

By the term "carrier material" is meant, for the purposes of the specification and claims to refer to sensitive documents, checks, bank cards, credit cards, controlled access cards, currency, passports, visas, tickets, driver's licenses, personal identification cards, stock certificates, fine art (including paintings and sculptures), goods or items wherein the distribution or localization of which is desirably to be controlled by tracking, objects of commercial value, building materials, articles of clothing, packaging of goods, containers, machine parts, toys, body tissue (i.e., in applications such as tatoos, or identification of individual animals in a colony), items of manufacture, containers for goods, polymeric materials (including beads, polymeric biosensors, and the like), inorganic materials, and organic materials. A carrier material of the aforementioned carrier materials may be used in a preferred embodiment, and a preferred carrier material may be used separately in the method according to the present invention to the exclusion of carrier materials other than the preferred carrier material.

By the term "reactive functionality" is meant, for purposes of the specification and claims to refer to a compound or moiety that acts to operably link two different molecules. As known to those skilled in the art, and as will be more apparent by the following embodiments, there are several methods and compositions in which two or more molecules may be operably linked utilizing reactive functionalities. Reactive functionalities include, but are not limited to, bifunctional reagents, linker molecules "linker"), biotin, avidin, free chemical groups (e.g., thiol, or carboxyl, hydroxyl, amino, amine, sulfo, etc.), and reactive chemical groups (reactive with free chemical groups). A reactive functionality of the aforementioned reactive functionalities may be used in a preferred embodiment, and a preferred reactive functionality may be used separately in the method according to the present invention to the exclusion of reactive functionalities other than the preferred reactive functionality.

By the term "operably linked" is meant, for purposes of the specification and claims to refer to fusion or bond or an association, of sufficient stability to withstand conditions encountered in common usage of the carrier material, between a combination of different molecules or materials such as, but not limited to, between the quantum dot and a capping compound, between a capping compound and a diaminocarboxylic acid, between a diaminocarboxylic acid and a diaminocarboxylic acid, between a diaminocarboxylic acid and a linker, between a diaminocarboxylic acid and an amino acid, between an amino acid and an affinity ligand, between a water-soluble nanocrystal and a carrier material, and a combination thereof. As known to those skilled in the art, and as will be more apparent by the following embodiments, there are several methods in which reactive functionalities may be used for a combination to be operably linked.

By the term "linker" is meant, for purposes of the specification and claims to refer to a compound or moiety that acts as a molecular bridge to operably link two different molecules, wherein one portion of the linker is operably linked to a first molecule, and wherein another portion of the linker is operably linked to a second molecule. The two different molecules may be linked to the linker in a step-wise manner. There is no particular size or content limitations for the linker so long as it can fulfill its purpose as a molecular bridge. Linkers are known to those skilled in the art to include, but are not limited to, chemical chains, chemical compounds, carbohydrate chains, peptides, haptens, affinity ligands (e.g., antibodies, aptamers, lectins, oligonucleotides) and the like. The linkers may include, but are not limited to, homobifunctional linkers and heterobifunctional linkers. Heterobifunctional linkers, well known to those skilled in the art, contain one end having a first reactive functionality to specifically link a first molecule, and an opposite end having a second reactive functionality to specifically link to a second molecule. The linker may further comprise a protective group which blocks reactivity with a functional group on the linker which is used to react with and bind to a molecule to be linked. A deprotection reaction may involve contacting the linker to one or more conditions and/or reagents which removes the protective group, thereby exposing the functional group to interact with the molecule to be linked. Depending on the nature of the protective group, deprotection can be achieved by various methods known in the art, including, but not limited to photolysis, acidolysis, hydrolysis, and the like. Depending on such factors as the molecules to be linked, and the conditions in which the method of detection is performed, the linker may the linker may vary in length and composition for optimizing such properties as flexibility, stability, and resistance to certain chemical and/or temperature parameters. For example, short linkers of sufficient flexibility include, but are not limited to, linkers having from about 2 carbin atoms to about 10 carbon atoms. A linker of the aforementioned linkers may be used in a preferred embodiment, and a preferred linker may be used separately in the method according to the present invention to the exclusion of linkers other than the preferred linker.

Functionalizing water-soluble quantum dots with one or more reactive functionalities. In a first method, water-soluble quantum dots with a carboxylate-terminated capping group are operably linked to a protein using a compound which facilitates a chemical association or bond formation between the water-soluble quantum dot and a protein (e.g., reactive towards both $NH_2$ and $CO_2H$). One such compound is 1-[3-(dimethylamino) propyl]-3-ethylcarbodiimide hydrochloride ("EDC") which functions to activate at least one reactive functionality (e.g., a carboxylate) to catalyze its reaction with another reactive functionality such as the amide group of a protein (the term "protein" also encompasses a pep-tide). For example, upon reaction of the EDC-activated carboxyl ate with an amide of a protein, the EDC is precipitated from the reaction in the form of urea. As apparent to those skilled in the art, the protein has no particular size, length or content limitations, so long as the protein can function to operably link to the carrier material desired to be linked. Such proteins will be apparent to those skilled in the art to include, but are not limited to, avidin, streptavidin, and their biotiri-binding derivatives/modified versions (e.g., neutravidin, nitro-avidin, nitro-streptavidin, aceylated avidin, and the like). For purposes of brevity of description, but not limitation, avidin or streptavidin or their biotin-binding derivatives/modified versions will be referred to hereinafter as "avidin". In an illustrative embodiment, water-soluble quantum dots were formed by coating with li-mercaptoundecanoic acid, and deprotonating with potassium-t-butoxide. The carboxylated quantum dots were then esterified by treatment with EDC followed by sulfo-N-hydroxy-succinimide (sNHS). These quantum dots were then contacted with avidin under sufficient conditions to form an amide bond between the EDC-activated carboxylate of the quantum dot and the amine groups on avidin; thereby forming avidinylated, water-soluble quantum dots. The avidinylated, water-soluble quantum dots can then be contacted with and operably linked to a carrier molecule having one or more free biotin molecules (including native biotin or a biotin derivative having avidin-binding activity; e.g., biotin dimers, biotin multimers, carbo-biotin, and the like). Using methods known to those skilled in the art, biotin molecules can be added to or incorporated by derivatization of the protein via lysine e-amino groups, or via thiol groups generated by reduction of cysteines (see, e.g., U.S. Pat. No. 5,756,685).

In another embodiment, the functionalized quantum dots of the present invention are produced using reactive functionalities comprising thiol group and thiol reactive groups. One illustration of this embodiment involves use of maleimide derivatives. For example, CdX core/YZ shell quantum dots are overcoated with mercapto-functionalized amines (e.g., aminoethanethiol-HCl, homocysteine, or 1-amino-2-methyl-2-propanethiol-Hcl). Thus, the overcoating comprises a cap with amino groups. To these amino group-capped quantum dots are added (either in the presence or absence of FDC) a maleimide derivative that reacts with amino groups. Such a maleimide derivative may include, but is not limited to 3-maleimidopropionic acid N-hydroxysuccinimide ester, 3-maleimidopropionic acid, 3-maleimidobenzoic acid N-hydroxysuccinimide ester, 4-(maleimidomethyl)-1-cyclohexanecarboxylic acid N-hydroxysuccinimide ester. The resultant quantum dots, having a thiol-reactive group, can interact with and bind to carrier materials having been previously derivatized with one or more thiol groups. The resultant quantum dots, having a thiol-reactive group, can interact with and form thioether bonds in operably linking to the carrier material having one or more thiol groups. A carrier material comprising protein may be derivatized to contain one or thiol-reactive groups using methods known to those skilled in the art. In one method, a hetero-bifunctional crosslinking reagent (e.g., SMCC-succinimidyl 4-(N-maleimidomethyl) cyclohexane-1-carboxylate; or SPDP -succinimidyl 3-(2-pyridyldithio)propionate) can introduce thiol-reactive groups in a protein (see, e.g., U.S. Pat. Nos. 5,672,683, and 5,256,395; the disclosures of which are herein incorporated by reference).

In another embodiment, the functionalized quantum dots of the present invention are produced utilizing reactive functionalities comprising amino groups and amino reactive groups. One illustration of this embodiment involves overcoating CdX core/YZ shell quantum dots with mercapto-functionalized amines (e.g., aminoethane-thiol-HCl, homocysteine, or 1-amino-2-methyl-2-propanethiol-HCl) Thus, the overcoating comprises a cap with amino groups. To these amino group-capped quantum dots are contacted, and operably linked, a carrier material which has been previously derivatized with one or more amino reactive groups. Amino reactive groups are known to those skilled in the art to include, but are not limited to, active ester groups, haloacetyl groups, azide groups, isocyanate groups, isothiocyanate groups, and acid anhydride groups (see, e.g., U.S. Pat. No. 5,580,923, the disclosure of which is herein incorporated by reference).

By the term "diaminocarboxylic acid" is meant, for purposes of the specification and claims to refer to an amino acid that has two free amine groups. The amino acid may be a naturally occurring amino acid, a synthetic amino acid, a modified amino acid, an amino acid derivative, an amino acid precursor (e.g., citrulline and ornithine are intermediates in the synthesis of arginine), or a combination thereof. In a preferred embodiment, the diaminocarboxylic acid contains neutral (uncharged) polar functional groups which can hydrogen bond with water, thereby making the diaminocarboxylic acid (and the quantum dot to which it is made a part of) relatively more soluble in aqueous solutions containing water than those with nonpolar functional groups. Additionally, the diaminocarboxylic acid imparts one or more functional advantages to the water-soluble nanocrystal of which it is a part, as will be more apparent from the following embodiments Exemplary diaminocarboxylic acids include, but are not limited to, lysine, asparagine, glutamine, arginine, citrulline, ornithine, 5-hydroxylysine, djenkolic acid, β-cyanoalanine, a synthetic diaminocarboxylic acid (e.g., such as 3,4-diaminobenzoic acid, 2,3-diaminopropionic acid, 2,4-diaminobutyric acid, 2,5-diaminopentanoic acid, 2,6-diaminopimelic acid), and a combination thereof. A diaminocarboxylic acid of the aforementioned diaminocarboxylic acids may be used in a preferred embodiment, and a preferred diaminocarboxylic acid may be used separately in the method according to the present invention to the exclusion of diaminocarboxylic acids other than the preferred diaminocarboxylic acid.

By the term "amino acid" is meant, for purposes of the specification and claims to refer to a molecule that has at least one free amine group and at least one free carboxyl group. The amino acid may have more than one free amine group, or more than one free carboxyl group, or may further comprise one or more free chemical reactive groups other than an amine or a carboxyl group (e.g., a hydroxyl, a sulfhydryl, etc.). The amino acid may be a naturally occurring amino acid, a synthetic amino acid, a modified amino acid, an amino acid derivative, and an amino acid precursor. The amino acid may further be selected from the group consisting of a monoaminocarboxylic acid, and a diaminocarboxylic acid. In a preferred embodiment, the monoaminocarboxylic acid contains one or more neutral (uncharged) polar functional groups which can hydrogen bond with water, thereby making the monoaminocarboxylic acid (and the quantum dot to which it is made a part of) relatively more soluble in aqueous solutions containing water than those with non-polar functional groups. Exemplary monoaminocarboxylic acids include, but are not limited to, glycine, serine, threonine, cysteine, β-alanine, homoserine, γ-aminobutyric acid, and a combination thereof. An amino acid of the aforementioned amino acids may be used in a preferred embodiment, and a preferred amino acid may be used separately in the method according to the present invention to the exclusion of amino acids other than the preferred amino acid.

Another feature of the quantum dots used in the present invention is that the Cdx quantum dots are passivated with an overlayering ("shell") uniformly deposited thereon. The shell is preferably comprised of YZ wherein Y is Cd or Zn, and Z is S, or Se. Quantum dots having a CdX core and a YZ shell have been described in the art (see. e.g., Danek et al., 1996, *Chem. Mater.* 8:173–179; Dabbousi et al., 1997, *J. Phys. Chem.* B 101:9463; Rodriguez-Viejo et al., 1997, *Appi. Phys. Lett.* 70:2132–2134; Peng et al., 1997, *J. Am. Chem. Soc.* 119:7019–7029; 1996, *Phys. Review* B.53: 16338–16346; Bruchez, Jr. et al., 1998, *Science* 281:2013–2015; Chen and Nie, 1998, *Science* 281:2016–2018; the disclosures of which are hereby incorporated by reference). Another feature of the quantum dots used in the present invention is that they are water-soluble. "Water-soluble" is used herein to mean sufficiently soluble or suspendable in a aqueous-based solution including, but not limited to, water, water-based solutions, buffer solutions, and solutions or liquids used in manufacturing processes, as known by those skilled in the art. Typically, CdX core/YZ shell quantum dots are overcoated with trialkylphosphine oxide, with the alkyl groups most commonly used being butyl and octyl. One method to make the CdX core/YZ shell quantum dots water-soluble is to exchange this overcoating layer with one which will make the quantum dots water-soluble. For example, a mercaptocarboxylic acid is used to exchange with the trialkylphosphine oxide. Exchange of the capping group is accomplished by treating the water-insoluble quantum dots with a large excess of mercaptocarboxylic acid, either neat (e.g., at 60° C.) or in $CHCl_3$ solution (Chan et al, 1998, supra), followed by extraction into water. The thiol group of the new capping ligand forms Cd (or Zn)—S bonds, creating a coating which is not easily displaced in solution. This is an improvement over the use of trialkyphosphine oxide, in which the capping ligand form a dative bond between the oxide and the cadmium (or zinc). These ligands are readily displaced in the presence of other Lewis bases such as pyridine. In addition, the carboxylic acid moiety imparts water solubility to the quantum dots. Quantum dots capped with trialkylphosphine oxide are soluble only in organic, non-polar (or weakly polar) solvents. Another method to make the CdX core/YZ shell quantum dots water-soluble is by the formation of a layer of silica around the dots (Bruchez et al., 1998, supra) which affords nanocrystals with a spectral range of 400 nm to 2 μm in the peak emission, with typical emission widths of 20 to 30 nm [full width at half maximum (FWHM)], no red tail, and a broad continuous excitation spectrum. An extensively polymerized polysilane shell imparts waxer solubility to nanocrystalline materials, as well as allowing further chemical modifications of the silica surface. Another method to make CdX core/YZ shell quantum dots water-soluble is to overcoat the quantum dots with mercapto-functionalized amines (e.g., aminoethanethiol-HCl, homocysteine, or 1-amino-2-methyl-2-propanethiol-HCl). Preferably, these water-soluble quantum dots, before being functionalized, have a substantially uniform size in the range of sizes of a minimum of from less than or equal to about 1 nm, to a maximum of about 20 nm. Exemplary capping compounds include, but are not limited to, mercaptofunctionalized amines (e.g., aminoethanethiol-HCl, homocysteine, or 1-amino-2-methyl-2-propanethiol-HCl), or a combination thereof. A capping compound of the aforementioned capping compounds may be used in a preferred embodiment, and a preferred capping compound may be used separately in the method according to the present invention to the exclusion of capping compounds other than the preferred capping compound.

By the term "capping compound" is meant, for purposes of the specification and claims to refer to a compound having the formula $HS(CH_2)_nX$, wherein X is a carboxylate (carboxylic moiety). "n" is a number in the range of from 1 to about 20, and preferably greater than 4. The thiol group of the capping compound forms Cd (or Zn)—S bonds (depending on whether the shell is Cd or Zn), creating a layer which is not easily displaced in solution. This is an improvement over the use of a capping layer comprised of trialkylphosphine oxide ("TOPO"), in which a dative bond is formed between the oxide and the cadmium (or zinc); and which is readily displaced in the presence of other Lewis bases such as pyridine. Additionally, the carboxylic acid moiety of the capping compound imparts water solubility to the quantum dots. Exemplary capping compounds include, but are not limited to, mercaptocarboxylic acid, or mercaptofunctionalized amines (e.g., aminoethanethiol-HCl, homocysteine, or 1-amino-2-methyl-2-propanethiol-HCl), or a combination thereof. A capping compound of the aforementioned capping compounds may be used in a preferred embodiment, and a preferred capping compound may be used separately in the method according to the present invention to the exclusion of capping compounds other than the preferred capping compound.

By the term "functionalized nanocrystals" is meant, for purposes of the specification and claims to refer to water-soluble nanocrystals comprised of (in order from inner core to outward coatings or layers): a core of CdX wherein X is Se or Te or S; passivated with a shell preferably comprised of YZ wherein Y is Cd or Zn, and Z is S, or Se; coated with a capping compound; with least one additional coating comprising amino acid that functionalizes the nanocrystal, wherein each coating of amino acid contains neutral (uncharged) polar functional groups which can hydrogen bond with water, and may further comprise one or more free chemical reactive groups. In a preferred embodiment, the at least one layer of amino acid that functionalizes the nanocrystal is comprised of a coating of diaminocarboxylic acid; and additional layers thereon, if any, may be comprised of amino acid. Additionally, the functionalized nanocrystal may further comprise one or more linker molecules ("linker") which is operably linked to the outermost amino acid layer, wherein the linker is used to operably link the functionalized nanocrystal to the carrier material.

By the term "effective amount" is meant, when used in conjunction with water-soluble nanocrystals, for purposes of the specification and claims, to refer to an amount of water-soluble nanocrystals sufficient to contact the carrier material which, when excited with an appropriate excitation wavelength, will emit fluorescence emission of sufficient intensity for detecting and/or imaging a carrier material containing a code pattern comprised of the water-soluble nanocrystals. As apparent to one skilled in the art, such an amount will vary depending on factors which include, but are not limited to, the amount of water soluble nanocrystals operably linked to the carrier material, the sensitivity of the system used for detecting and/or imaging the labeled carrier material, and any physical properties associated with the carrier material itself that may affect the detection of operably linked water-soluble nanocrystals (e.g., autofluorescence, or quenching).

By the term "water-soluble nanocrystals" is meant, for purposes of the specification and claims to refer to nanocrystals comprised of (in order): a core of CdX wherein X is Se or Te or S; passivated with a shell preferably comprised of YZ wherein Y is Cd or Zn, and Z is S, or Se; and a capping compound. In a preferred embodiment, the water-soluble nanocrystals further comprise functionalized nanocrystals, as will be more apparent from the following descriptions. A preferred water-soluble nanocrystal (i.e., functionalized nanocrystals) may be used separately in the method according to the present invention to the exclusion of water-soluble nanocrystals other than the preferred water soluble nanocrystals.

Conventional fluorescent labels generally suffer from short-lived fluorescence; e.g., undergo photobleaching after minutes of exposure to an excitation light source. Thus, they would not be suitable for imaging and/or detection requiring any significant length of time, as may be needed for purposes of identification or verification of a carrier material. Further, conventional fluorescent labels are sensitive to changes in environment which can decrease their quantum yield; e.g., brought about by changes in the surrounding pH and dissolved oxygen. Another disadvantage of conventional fluorescent labels is that typically the excitation spectrum of a species of fluorescent label may be quite narrow. However, even when a single light source is used to provide a single excitation wavelength (in view of the spectral line width), often there is insufficient spectral spacing between the emission optima of different species of fluorescent labels to permit individual and quantitative detection without substantial spectral overlap. Thus, when using a combination of different fluorescent labels, multiple filters are typically needed to detect the resultant emission spectra of the combination. Conventional fluorescent labels are limited in sensitivity and resolution of imaging due to the limitations of intensity, photobleaching, and the finite number of molecules which can be used to label a substrate.

The present invention relates to quantum dots that are produced so as to be water-soluble, and providing a carrier material with an identifiable code pattern comprised of water-soluble nanocrystals. In producing an identifiable code pattern according to the present invention, desirably the water-soluble nanocrystals: can be manufactured in relative monodispersity comprising a particular uniform size, and when excited with an excitation light source, emitted is a discrete fluorescence peak of narrow bandwidth (e.g., from about 20 nm to about 50 nm) and of a particular color; are between about 1 nanometers to about 20 nanometers in size; may be functionalized with one or more reactive functionalities to facilitate bonding to a carrier material; and when comprising multiple species, each species representing a distinct size range, can be excited with a single wavelength or wavelength spectrum of light, resulting in many emissions of colors that can be detected simultaneously and discretely. The quantum dots can be excited with a single wavelength of light resulting in a detectable luminescence emission of high quantum yield (e.g., a single quantum dot having at a fluorescence intensity greater than that of at least 10 rhodamine molecules) and with a discrete luminescence peak.

Quantum dots are comprised of a core of CdX wherein X is Se or Te or S. Such quantum dots are well known in the art. CdX quantum dots can be passivated with an overlayering ("shell") uniformly deposited thereon. A preferred passivating shell is comprised of YZ wherein Y is Cd or Zn, and Z is S, or Se. Quantum dots having a CdX core and a YZ shell have also been generally described in the art. However, a feature of the quantum dots used to operably link to a carrier material is that the nanocrystals are water-soluble. "Water-soluble" is used herein to mean that the nanocrystals are sufficiently soluble or suspendable in a aqueous-based solution including, but not limited to, water, water-based solutions, buffer solutions, that are used in manufacturing processes comprising operably linking water-soluble components to carrier materials, as known by those skilled in the art.

Typically, CdX core/YZ shell quantum dots are overcoated with trialkylphosphine oxide, with the alkyl groups most commonly used being butyl and octyl. One method to make the CdX core/YZ shell quantum dots water-soluble is to exchange this overcoating layer with one which will make the quantum dots water-soluble. For example, a mercaptocarboxylic acid is used to exchange with the trialkylphosphine oxide. Exchange of the capping group is accomplished by treating the water-insoluble quantum dots with a large excess of mercaptocarboxylic acid, either neat (e.g., at 60° C.) or in $CHCl_3$ solution (Chen and Nie, 1998, Science 281:2016–2018), followed by extraction into water. The thiol group of this capping compound forms Cd (or Zn)—S bonds, creating a coating which is not easily displaced in solution. This is an improvement over the use of trialkylphosphine oxide, which forms a dative bond between the oxide and the cadmium (or zinc), and which is readily displaced in the presence of other Lewis bases such as pyridine. In addition, the carboxylic acid moiety of the capping compound imparts some water solubility to the nanocrystals, whereas quantum dots capped with trialkylphosphine oxide are soluble only in organic, non-polar (or weakly polar) solvents. Another method to make the CdX core/YZ shell quantum dots water-soluble is by the formation of a layer of silica around the dots (Bruchez et al., 1998, Science 281:2013–2015). An extensively polymerized polysilane shell imparts water solubility to nanocrystalline materials, as well as allowing further chemical modifications of the silica surface. However, depending on the nature of the coating group, quantum dots which have been reported as water-soluble may have limited stability in an aqueous solution, particularly when exposed to air (oxygen) and/or light. More particularly, oxygen and light can cause the molecules comprising the coating to become oxidized, thereby forming disulfides which destabilize the attachment of the coating molecules to the shell. Thus, oxidation may cause the coating molecules to migrate away from the surface of the nanocrystals, thereby exposing the surface of the nanocrystals in resulting in "destabilized nanocrystals". Destabilized nanocrystals form aggregates when they interact together, and the formation of such aggregates eventually leads to irreversible flocculation of the nanocrystals. Additionally, carboxylate groups can cause non-specific binding to a carrier material, particularly to an area of the carrier material which is not intended or not desirable to be operably linked to a water-soluble nanocrystal. Thus, in one embodiment of providing an identifiable code pattern according to the present invention, the water-soluble nanocrystals consist essentially of a core of CdX wherein X is Se or Te or S; the core is then passivated with a shell preferably comprised of YZ wherein Y is Cd or Zn, and Z is S, or Se; and the shell is overlayed with a capping compound. However, it has been discovered that such water-soluble nanocrystals have disadvantages, as will be more apparent from the following descriptions (see also, FIGS. 2 and 3). Hence, in a preferred embodiment of applying water-soluble nanocrystals providing an identifiable code pattern according to the present invention, the water-soluble nanocrystals comprises functionalized nanocrystals.

EXAMPLE 1

In this embodiment is illustrated the production of exemplary water-soluble nanocrystals comprising a CdSe core, and a ZnS shell, "(CdSe)ZnS", and a layer of capping compound. TOPO capped CdSe were produced by placing TOPO (5 g) in a vessel, and dried at 150° C. for 1 hour under vacuum. The vessel was then backfilled with argon and heated to 300° C. In a controlled environment, $CdMe_2$ (7.2 μl, 0.1 mmol) and 1 M trioctylphosphine-Se solution (90 μl, 0.09 mmol) and trioctylphosphine (5 ml) were mixed, and then placed into an injector. This mixture was added to the TOPO in a reaction vessel, previously removed from the heat, in a single continuous injection with vigorous stirring, thereby resulting in the temperature decreasing to about 180° C. The reaction vessel was then subjected to heat to raise the temperature 5° C. every 10 minutes. Aliquots may be removed from the reaction vessel at various time intervals (5 to 10 minutes) to monitor the increase in size of nanocrystals over time, by the observation of the absorption spectra. The temperature may be changed, or the reaction halted, upon reaching nanocrystals of the desired characteristics. For example, the reaction vessel was cooled to about 60° C., 40 ml of methanol was added to cause the nanocrystals to flocculate. After centrifugation, a brightly colored liquid layer of nanocrystals dissolved in trioctylphosphine remained. The methanol/TOPO layer was decanted off, and pyridine (10 ml) was added to the nanocrystal solution and allowed to stand for at least one hour. The nanocrystals were then precipitated as a powder by addition of hexanes, and separated by centrifugation. The powder was washed once more with hexanes, then dissolved in 30 ml pyridine, and centrifuged to remove any reaction byproducts.

To prepare (CdSe)ZnS nanocrystals, the pyridine solution (30 ml) was placed in a reaction vessel, rigorously degassed with an inert gas (e.g., argon), and refluxed for one hour before adjusting the temperature to approximately 100° C. Equimolar amounts of diethyl zinc (zinc source) and hexamethyldisilathiane (sulfide source) were dissolved in trioctylphosphine (2–4 ml) in a controlled environment (glove box) and loaded into an injector. A reaction vessel containing the CdSe dots dispersed in pyridine was heated under an atmosphere of argon, and the Zn and S were added dropwise, via the injector, with vigorous stirring of the mixture for 5–10 minutes. The mixture was left stirring for several hours. After cooling, the pyridine solution was centrifuged to remove any insoluble material. The passivated nanocrystals were stored in this solution to ensure that the surface of the nanocrystals remained passivated with pyridine.

To prepare nanocrystals which are water-soluble, the pyridine overcoating of the (CdX) core/YZ shell nanocrystals were exchanged with a capping compound which contributes to the water-solubility of the resultant nanocrystals. For example, a capping compound comprising mercaptocarboxylic acid may be used to exchange with the pyridine overcoat. Exchange of the coating group is accomplished by treating the water-insoluble, pyridine-capped quantum dots with a large excess of neat mercaptocarboxylic acid. To accomplish this, the pyridine-capped (CdSe)ZnS quantum dots were precipitated with hexanes, and then isolated by centrifugation. The residue was dissolved in neat mercaptoacetic acid, with a few drops of pyridine added, if necessary, to form a transparent solution. The solution is allowed to stand at room temperature for at least six hours. Longer incubation times lead to increased substitution by the thiol. Overnight incubations are ideal. Chloroform is added to precipitate the nanocrystals and wash away excess thiol. The nanocrystals were isolated by centrifugation, washed once more with chloroform, and then washed with hexanes. The residue was briefly dried with a stream of argon. The resultant nanocrystals, coated with the capping compound, were then soluble in water or other aqueous solutions. The nanocrystals, in an aqueous solution, were centrifuged once more, filtered through a 0.2 μm filter, degassed with argon, and stored in an amber vial. Failure to protect the nanocrystals, in solution, from air and light leads to irreversible flocculation, usually within a week. Although proper storage conditions may extend the shelf life of these water-soluble nanocrystals, there is a drawback because of their sensitivity to oxidation, and a need for repeatedly degassing the vial after each use. As mentioned previously, oxidation may result in the capping compound becoming destabilized; and destabilization can result in irreversible flocculation of the nanocrystals.

EXAMPLE 2

Figure 1:
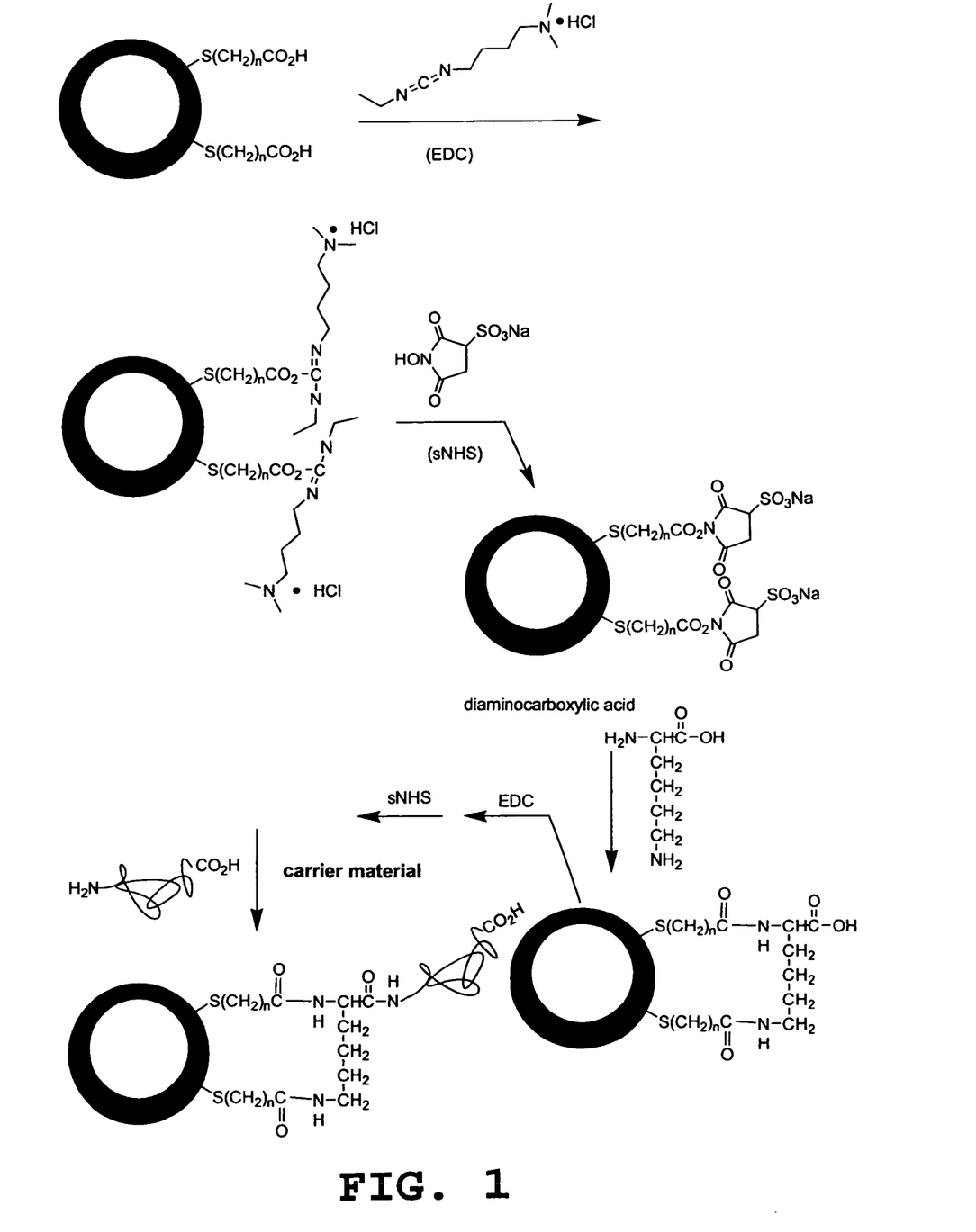
FIG. 1. is a schematic illustrating chemically modifying a water-soluble nanocrystal containing a layer of a capping compound to further comprise a layer of a diaminocarboxylic acid, and then operably linking the diaminocarboxylic acid to a carrier material.

Illustrated in this embodiment is the production of exemplary water-soluble nanocrystals comprising functionalized nanocrystals. Water-soluble nanocrystals were produced using the methods illustrated in Example 1. The water-soluble nanocrystals were functionalized by a coating comprising operably linking organic molecules comprising a diaminocarboxylic acid to the capping compound in forming a functionalized nanocrystal. In a preferred embodiment, the diaminocarboxylic acid (a) contributes to the water-solubility of the functionalized nanocrystal because it has polar functional groups which can hydrogen-bond with water; (b) has at least two free functional groups which are carboxyl-reactive, thereby enabling the diaminocarboxylic acid molecule to operably link to, and may crosslink, carboxyl groups extending from the capping compound on the capped nanocrystals; (c) once operably linked to the capping compound, has one or more free functional groups which can be used for operably linking to a carrier molecule or to a linker which is then operably linked to a carrier molecule; and (d) provides other beneficial properties to the resultant functionalized nanocrystals. A preferred diaminocarboxylic acid comprises lysine. For example, and as illustrated in FIG. 1, mercaptoacetic acid-capped nanocrystals were dissolved in an aqueous buffer system (pH of about 7). The buffer may comprise such buffers as PBS or HEPES; however, the presence of phosphate may dramatically decrease the lifetime of the cross-linking agent. To the capped nanocrystals was added EDC (1-ethyl-3-[3-dimethyl-aminopropyl] carbdiimide) and sulfoNHS (sulfo-N-hydroxy-succinimide) in 500–1000 times excess. The resulting solution was stirred at room temperature for 30 minutes. Mercaptoethanol was added to neutralize unreacted EDC at 20 mM concentration, followed by stirring for 15 minutes. The entire solution was then added dropwise, with stirring, to a solution of lysine (large excess) in the same buffer; and the mixture was stirred for 2 hours at room temperature. Ethanolamine (30 mM) was added to quench the reaction; and the mixture was stirred for 30 minutes at room temperature or left overnight at 4° C. The solution was centrifuged to remove any precipitated solids, and then ultrafiltered through a 30 kD MW centrifugal filter. The resultant concentrated, functionalized nanocrystals can be solubilized in an aqueous solution of choice.

In another embodiment, as also illustrated in FIG. 1, the coating comprising diaminocarboxylic acid of the functionalized nanocrystals is then operably linked to a carrier material, or to a linker which is then operably linked to the carrier material. For example, depending on factors such as the species of diaminocarboxylic acid and/or the amount of diaminocarboxylic acid which is used to operably link to the capping compound, the operably linked diaminocarboxylic may have one or more reactive functionalities (e.g., free amino group, free carboxyl group, and a combination thereof) that can be used to operably link to a reactive functionality of the carrier material (or to a linker). As an illustrative example, a carrier material comprises a polymeric material. The polymeric material may comprise commercially available beads such as carboxyl acrylic beads, carboxylate modified polystyrene, latex beads, or amino-modified polystyrene beads. In continuing with this example, a polymeric material having free carboxyl-reactive groups (e.g., amine groups) can be operably linked to free carboxyl groups of the molecules of diaminocarboxylic acid comprising a coating of the functionalized nanocrystals using methods known in the art (e.g., treatment with EDC, followed by treatment with sulfo-NHS, as previously described herein). In an alternative, a polymeric material having free amino-reactive groups (e.g., carboxyl groups) can be operably linked to free amino groups of the molecules of diaminocarboxylic acid comprising a coating of the functionalized nanocrystals using methods known in the art. The beads complexed to the functionalized nanocrystals may then be deposited in an array of spots, or flowed through a detection system, in providing an identifying code pattern. If desirable, essentially the same procedure can be used to operably link an additional amino acid layer onto the diaminocarboxylic acid layer, and then to operably link the resultant functionalized nanocrystal to a carrier material.

Figure 2:
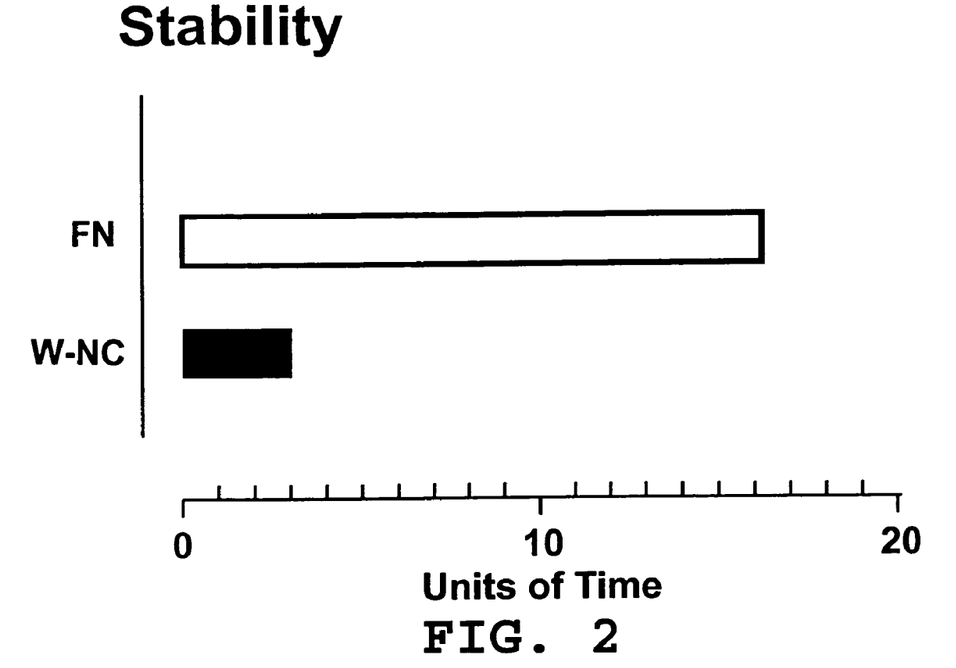
FIG. 2 is a bar graph comparing the stability of water-soluble nanocrystals ("W-SN") to the stability of functionalized nanocrystals ("FN") under oxidizing conditions.
Figure 3:
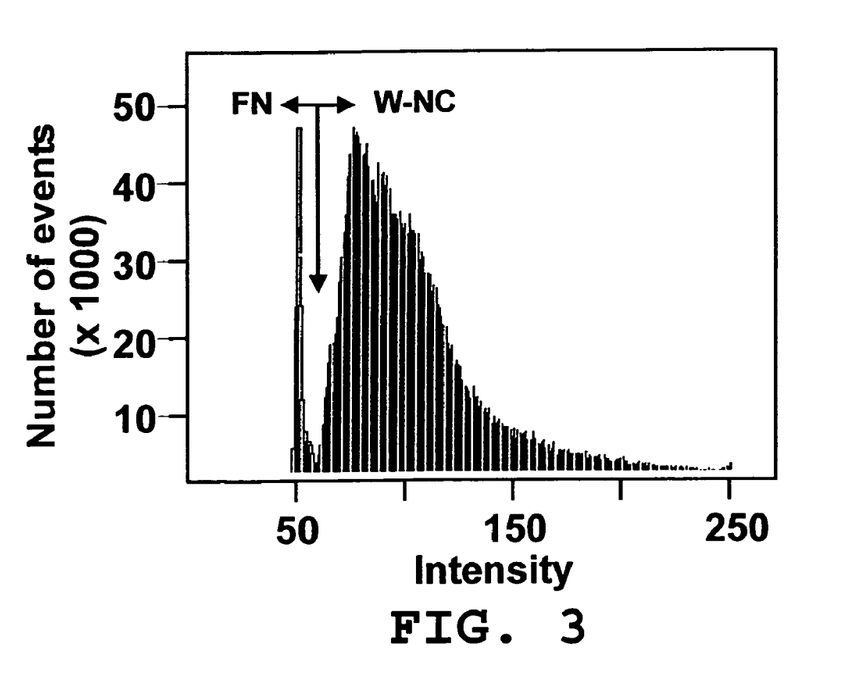
FIG. 3 is a bar graph comparing the non-specific binding of water-soluble nanocrystals ("W-SN") to the non-specific binding of functionalized nanocrystals ("FN").

Regarding stability, as shown in FIG. 2, the functionalized nanocrystals containing a coat of diaminocarboxylic acid ("FN") unexpectedly show a significant increase in stability in an aqueous environment compared to water-soluble nanocrystals having an outer layer of just the capping compound ("W-SN"), when exposed over time to identical conditions of an oxidizing environment (e.g., light and air). Additionally, as shown in FIG. 3, functionalized nanocrystals containing a coat of diaminocarboxylic acid ("FN") unexpectedly result in a significant decrease in non-specific binding compared to water-soluble nanocrystals having an outer layer of just the capping compound ("W-SN"), when each were contacted with a surface that is both hydrophilic and hydrophobic, followed by washing of the surface, followed by detection of residual nanocrystals (as measured by number of events of fluorescence versus the intensity of fluorescence; using a fluorescence microscope with a video camera attachment, time of exposure—$1/30^{th}$ of a second).

EXAMPLE 3

In this example is disclosed various embodiments for providing a carrier material with an identifiable code pattern by applying combinations of water-soluble nanocrystals comprised of an effective amount of water-soluble nanocrystals. In a preferred embodiment, the water-soluble nanocrystals comprise an effective amount of functionalized nanocrystals. In another embodiment, the water-soluble nanocrystals comprise a combination of water-soluble nanocrystals which do not comprise functionalized nanocrystals, and functionalized nanocrystals. In the method of present invention, applied (e.g., one or more of incorporating, affixing, appending, depositing, localizing, and the like) to a carrier material is an identifiable code pattern comprising one or more species (depending on if a single color or multiple colors is desired) of water-soluble nanocrystals by contacting the water-soluble nanocrystals to the carrier material in operably linking the water-soluble nanocrystals to the carrier material. For example, in producing the identifiable code pattern, "applied to the carrier material" means that the water-soluble nanocrystals may be incorporated into the carrier material; or may be used as a component in the formation of the carrier material; or may be added to a surface of the carrier material; or be added to a composition which is then applied to the carrier material; or a combination thereof. The pattern may comprise a format selected from the group consisting of one or more designs, one or more letters, one or more numbers, one or more symbols, one or more lines, one or more characters, encoded data, and a combination thereof. A preferred pattern may be used to the exclusion of a pattern other than the preferred pattern.

In one preferred embodiment, in providing an identifiable code pattern, the water-soluble nanocrystals may be incorporated into the structure of the carrier material. In another preferred embodiment, the water-soluble nanocrystals may be linked to the carrier material via one or more reactive functionalities or via a linker. In another preferred embodiment, the water-soluble nanocrystals may be applied to the surface of the carrier material such as being applied as a component in a, or comprising a, paint, fiber, ink, print, polymer, or decal. In another preferred embodiment, the water-soluble nanocrystals may be applied to a carrier material comprising an accessory, which is then attached to the goods to be identified or authenticated or verified, and wherein the accessory may be in the form of a label, tag, sticker, or combination thereof. For example, incorporation of water-soluble nanocrystals into a carrier material can be achieved by various methods known to those skilled in the art. As apparent to one skilled in the art from the descriptions herein, the method for incorporating water-soluble nanocrystals into a carrier material will depend on such factors as the nature of the carrier material, the processes of manufacturing or modifying the carrier material to incorporate the water-soluble nanocrystals, and the format of the identifiable code pattern desired to be produced. For example, the carrier material may be polymeric in nature, including, but not limited to nylon, polyesters, polyvinylchloride, polystyrene, polypropylene, polyurethanes, acetate resins, acrylic resins, and fluoro-carbons. The water-soluble nanocrystals may be blended together with or added to the polymeric carrier materials at conditions wherein the polymeric carrier material is in a liquid form or in a semi-solid, porous form. The mixture is then cooled or hardened, thereby resulting in a solid carrier material having incorporated therein the water-soluble nanocrystals in producing an identifiable code pattern.

Another embodiment of the method for providing an identifiable code pattern by applying water-soluble nanocrystals to a carrier material involves applying (e.g., in spray or droplet form) one or more solutions of water-soluble nanocrystals to a carrier material (e.g., using a single injector, or multiple injectors such as in an ink jet printer). The one or more solutions of water-soluble nanocrystals may be applied in a desired pattern or format onto the carrier material, and then the applied one or more solutions is dried (e.g., by evaporation or other suitable means) onto the carrier material. For example, the water-soluble nanocrystals may be suspended in an aqueous surfactant solution. In applying the resultant suspension to a carrier material having pores (e.g., fabric, paper, fibrous material, and the like), the surfactant allows the water-soluble nanocrystals to wick into the fibers of the carrier material. Thus, the identifiable code pattern may be observed within the fibers of the carrier material when using appropriate detection means. In an illustrating, but non-limiting example, a first solution may contain one uniform size of water-soluble nanocrystals (e.g., of a size that when excited will fluoresce a wavelength spectrum corresponding to the color orange), whereas an additional solution may contain water-soluble nanocrystals of a uniform size different than that contained in the first solution (e.g., of a size that when excited will fluoresce a wavelength spectrum corresponding to the color green). Additional solutions may comprise water-soluble nanocrystals representative of other colors, or combinations of colors (with respect to their fluorescence emissions). In providing an identifiable code pattern, the different solutions may be applied as separate solutions to the carrier material, or may be mixed in the application process; and may be applied simultaneously or at separate times to the carrier material.

Another embodiment of the method of providing an identifiable code pattern by applying water-soluble nanocrystals to a carrier material is to mix the water-soluble nanocrystals and carrier material together in the process of molding or casting the carrier material in a manner so as to achieve the desired identifiable code pattern. In another embodiment of the method for providing an identifiable code pattern by applying water-soluble nanocrystals to a carrier material, the water-soluble nanocrystals comprise a composition selected from the group consisting of a paint, ink, print, or dye. The water-soluble nanocrystals are mixed into a solution in forming the composition, and the composition is then applied onto or injected into the carrier material where it becomes affixed. The composition containing the water-soluble nanocrystals may be applied onto or injected into the carrier material in a controlled manner in forming a desired format so as to form an identifiable code pattern. If the composition further comprises a particular pigment that has properties which may interfere with the detection of the water-soluble nanocrystals, the pigment may be pre-treated to minimize such interference, e.g., by pretreatment with light absorbers. This embodiment is particularly pertinent to carrier materials such as canvas, paper, cardboard, posterboard, linen, fabric, other fibrous material, or plastic (e.g., as used to make a card having some identity function) to which is applied a pigmented composition that further comprises water-soluble nanocrystals.

Figure 4:
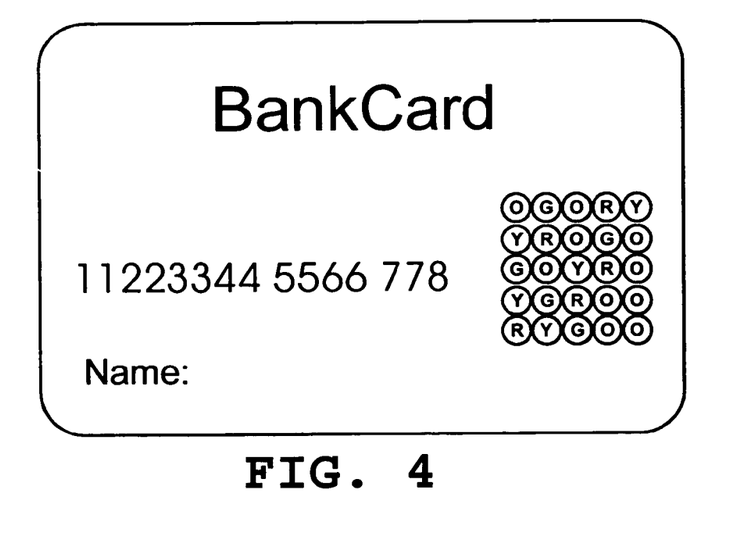
FIG. 4 is a schematic illustration of an identifiable code pattern, associated with a card, comprised of separate deposits or localizations of water-soluble nanocrystals of different uniform sizes which enable a detectable and identifiable pattern comprised of multiple colors.
Figure 5:
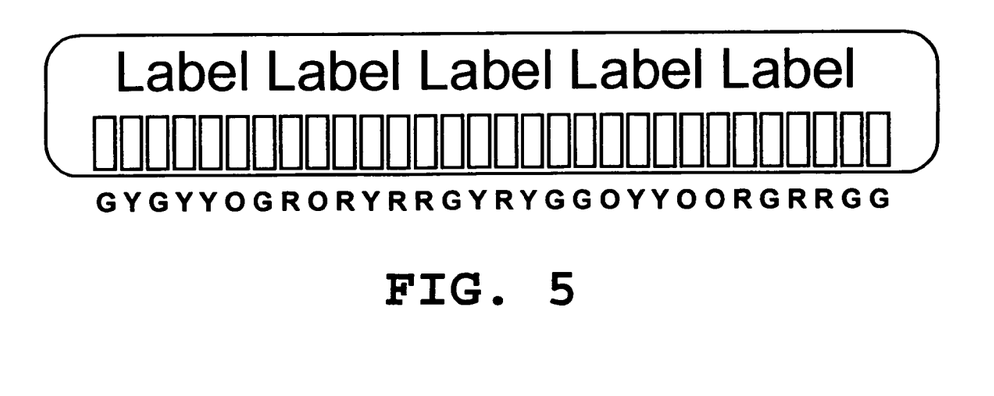
FIG. 5 is a schematic illustration of an identifiable code pattern comprised of separate deposits or localizations of water-soluble nanocrystal of different uniform sizes which enable a detectable and identifiable pattern comprised of multiple colors.

In a preferred embodiment of providing an identifiable code pattern to a carrier material, a plurality of species (each species comprising a uniform size that is different than the uniform size of other species applied) of water-soluble nanocrystals are contacted with the carrier material in operably linking the water-soluble nanocrystals to the carrier material for the purpose of providing an identifiable code pattern comprising more than one color. In one example of this embodiment, each species of water-soluble nanocrystals are contained in separate solutions; i.e., each solution comprises a suspension of a water-soluble nanocrystals of a substantially uniform size. Thus, for example, a first solution comprises a suspension of water-soluble nanocrystals that will fluoresce yellow when excited (FIGS. 4 and 5: "Y"); a second solution comprises water-soluble nanocrystals that will fluoresce green when excited (FIGS. 4 and 5, "G"); and a third solution comprises water-soluble nanocrystals that will fluoresce orange when excited (note, "first", "second", and "third" are used for the purpose of distinction, and not for the express purpose of designation of order in application). As illustrated in FIGS. 4 and 5, each separate solution, when applied to the carrier material, may form a separate deposit or localization of the water-soluble nanocrystals in forming an identifiable code pattern. Thus, for example, the resultant identifiable code pattern may be comprised of a spatial arrangement of deposits or localizations of water-soluble nanocrystals that enable an identifiable code pattern detectable as multiple colors (see, e.g., FIGS. 4 and 5, "Y", "G", "O"). Water-soluble nanocrystals representative of other colors of the spectrum may be used as well. The separate solutions may either be separately applied to the carrier material, or they may be applied in a simultaneous manner to the carrier material. As illustrated in FIG. 4, he identifiable code pattern may comprise a format comprising one or more designs, one or more letters, one or more numbers, one or more symbols, one or more characters, encoded data, and a combination thereof. As illustrated in FIG. 5, the identifiable code pattern comprises encoded data which can be decoded by the detection system in a process of identifying or tracking the carrier material. The encoded data may comprise data matrix symbols, UPC symbols, binary data, alphanumeric data, textual data, numeric data, data representative of localization parameters, and data encoded in other formats, or a combination thereof; any or all of which may be in machine readable format.

The identifiable code pattern may comprise a spatial arrangement of deposits or localizations of water-soluble nanocrystals in a format that may be made unique to the carrier material to which it is applied; and which can be rendered detectable and readable by exposure of that portion of the carrier material provided with the identifiable code pattern to an excitation light source. Detection of the identifiable code pattern, after exposure to such a light, may be by a detection system comprising a scanner or reader or other analytical instrument which can detect fluorescence peaks in the spectral range of about 410 nm to about 750 nm; and, optionally (when the pattern comprises more than one color of emitted fluorescence), distinguish between discrete fluorescence peaks within that spectral range. The detection system may further comprise a computer or data processor which can perform one or more functions including, but not limited to, imaging the detected identifiable code pattern, storing the detected identifiable code pattern; decoding the information represented by the detected identifiable code pattern and storing the information decoded therefrom; comparing the detected identifiable code pattern (or information decoded therefrom) to a database of identifiable code patterns for a purpose selected from the group consisting of verifying the detected identifiable code pattern, authenticating the detected identifiable code pattern, authenticating information decoded from the detected identifiable code pattern, distinguishing the detected identifiable code pattern from other identifiable code patterns in determining localization parameters, and a combination thereof; and providing a warning signal (comprising a display or sound or a combination thereof) if the detected identifiable code pattern is not identifiable (i.e., is not verifiable, is not authentic, or is neither verifiable nor authentic). Computer units having some of these functions are known to those skilled in the art (see, e.g., U.S. Pat. No. 5,592,561, the disclosure of which is herein incorporated by reference). As known to those skilled in the art, the detection system should be able to detect and distinguish discrete fluorescence peaks that may be emitted by water-soluble nanocrystals, and may comprise one or more photodetectors, one or more filters, a charge couple device camera (CCD camera), a fluorescence microscope, a fluorescence cube, a scanner or reader, and a computer for processing the detected identifiable code pattern.

As will be apparent to those skilled in the art from the descriptions herein, the absorbance peak and fluorescence peak emission of the water-soluble nanocrystals depends on such factors which include, but are not limited to, the chemical nature of the water-soluble nanocrystal, and the size of the core/shell quantum dot. In a general illustrative but non-limiting example, CdSe/ZnS quantum dots having a diameter of about 68.4 angstroms (A) may be excited with light of a wavelength in the range of from about 400 nm to 500 nm, and emit a fluorescence peak (corresponding to the color orange) at 609 nm which may be detected using an appropriate detection system. CdSe/ZnS quantum dots having a diameter of about 53.2 A may be excited with light of a wavelength in the range of from about 400 nm to 500 nm, and emit a fluorescence peak (corresponding to the color yellow) at 545 nm which may be detected using an appropriate detection system. CdSe/ZnS quantum dots having a diameter of about 46.6 A may be excited with light of a wavelength in the range of from about 400 nm to 500 nm, and emit a fluorescence peak (corresponding to the color green) at 522 nm which may be detected using an appropriate detection system.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept, and therefore such modifications and/or adaptations are intended to be within the meaning and scope of the appended claims.

What is claimed is:

1. A method of providing a carrier material with an identifiable code pattern, the method comprising:
   applying an effective amount of one or more species of fluorescent water-soluble nanocrystals to the carrier material and operably linking the nanocrystals to the carrier material in an identifiable code pattern by linking reactive functionalities of the nanocrystal to the surface of the carrier material in a spatial arrangement, wherein the identifiable code pattern is used to determine the identity or authenticity of the carrier material.

2. The method according to claim 1, wherein the identifiable code pattern comprises a format selected from the group consisting of one or more designs, one or more letters, one or more numbers, one or more symbols, one or more characters, encoded data, and a combination thereof.

3. The method according to claim 1, wherein the fluorescent water-soluble nanocrystals are applied to a surface of the carrier material.

4. The method according to claim 1, wherein the one or more species of fluorescent water-soluble nanocrystals comprises a plurality of species of water-soluble nanocrystals, wherein each species comprises a uniform size that is different from the uniform size of other species of the plurality of species, in providing an identifiable code pattern that can be detected as comprising multiple colors.

5. An article comprising an identifiable code pattern comprising an effective amount of one or more species of fluorescent water-soluble nanocrystals, wherein the nanocrystals are operably linked to a carrier material in an identifiable code pattern by linking reactive functionalities of the nanocrystal to the surface of the carrier material in a spatial arrangement, the identifiable code pattern of the fluorescent water-soluble nanocrystals applied to the cater material comprises a format selected from the group consisting of one or more designs, one or more letters, one or more numbers, one or more symbols, one or more characters, encoded data, and a combination thereof, wherein the identifiable code pattern is used to determine the identity or authenticity of the carrier material.

6. The identifiable code pattern according to claim 5, wherein the one or more species of fluorescent water-soluble nanocrystals comprises a plurality of species of water-soluble nanocrystals, wherein each species comprises a uniform size that is different from the uniform size of other species of the plurality of species, in providing an identifiable code pattern that can be detected as comprising multiple colors.

7. A method of providing a carrier material with an identifiable code pattern, the method comprising:
   applying an effective amount of one or more species of fluorescent water-soluble nanocrystals to the carrier material and operably linking the nanocrystals with the carrier material in an identifiable code pattern by linking reactive functionalities of the nanocrystal to the surface of the carrier material in a spatial arrangement, said nanocrystals having a capping layer that includes amine, or carboxylic acid moieties;
   wherein the identifiable code pattern is used to determine the identity or authenticity of the carrier material.

8. The method according to claim 7, wherein the identifiable code pattern comprises a format selected from the group consisting of one or more designs, one or more letters, one or more numbers, one or more symbols, one or more characters, encoded data, and a combination thereof.

9. The method according to claim 7 wherein the carrier material is derivatized with amino reactive groups or carboxylic acid reactive groups.

10. An article comprising:
    an effective amount of one or more species of water-soluble fluorescent nanocrystals, the nanocrystals having a capping layer that includes amine or carboxylic acid moieties, the nanocrystals being operably linked by the capping layer to a carrier material in an identifiable code pattern by linking reactive functionalities of the nanocrystal to a surface of the carrier material in a spatial arrangement such that a determination of the identity or authenticity of the carrier material can be made.

11. The article of claim 10 wherein the identifiable code pattern includes a format selected from the group consisting of one or more designs, one or more letters, one or more numbers, one or more symbols, one or more characters, encoded data, and a combination thereof.

12. The article of claim 10, wherein the one or more species of water-soluble fluorescent nanocrystals includes a plurality of species of water-soluble nanocrystals, wherein each species includes a uniform size that is different from the uniform size of other species of the plurality of species, in providing an identifiable code pattern that can be detected as comprising multiple colors.

13. The article of claim 10 wherein the identifiable code pattern is machine readable.

* * * * *